US00PP35746P2

(12) United States Plant Patent
Valin

(10) Patent No.: US PP35,746 P2
(45) Date of Patent: Apr. 16, 2024

(54) SHRUB ROSE PLANT NAMED 'TMRO14-08'

(50) Latin Name: ***Rosa* x *hybrida***
Varietal Denomination: TMRO14-08

(71) Applicant: Branded Garden Products Ltd., Ipswich (GB)

(72) Inventor: Charles Valin, Ipswich (GB)

(73) Assignee: Branded Garden Products Ltd., Ipswich (GB)

( * ) Notice: Subject to any disclaimer, the term of this patent is extended or adjusted under 35 U.S.C. 154(b) by 0 days.

(21) Appl. No.: 18/186,172

(22) Filed: Mar. 19, 2023

(51) Int. Cl.
*A01H 5/02* (2018.01)
*A01H 6/74* (2018.01)

(52) U.S. Cl.
USPC ..... Plt./103
CPC ..... *A01H 6/749* (2018.05)

(58) Field of Classification Search
USPC ..... Plt./107, 103
CPC ..... A01H 5/02; A01H 5/0222
See application file for complete search history.

(56) References Cited

PUBLICATIONS https://online.flippingbook.com/view/753417629/; 2023; 3 pages.*
https://www.youtube.com/watch?v=M2FX8uUVrHl; Jun. 24, 2021; 1 page.*
https://vimeo.com/563780037; Jun. 16, 2021; 1 page.*

* cited by examiner

*Primary Examiner* — Kent L Bell
(74) *Attorney, Agent, or Firm* — Weatherly IP Solutions, LLC; James M. Weatherly

(57) ABSTRACT

A new cultivar of *Rosa* named 'TMRO14-08' that is distinguishable by a semi-prostrate plant habit, small glossy green compound leaves, and lightly fragrant semi-double flowers which open pale pink in color with darker pink centers. The pink color of the early flowers soon gives way to pure white flowers with occasional tinges of very pale pink. 'TMRO14-08' bears glossy red hips when mature and is hardy in USDA Hardiness Zone 5. In combination, these traits set 'TMRO14-08' apart from all other existing varieties of *Rosa* known to the inventor.

1 Drawing Sheet

Genus and species: *Rosa* x *hybrida*.
Denomination: 'TMRO14-08'.

BACKGROUND

The present invention comprises a new and distinct variety of rose, botanically known as *Rosa* x *hybrida* and hereinafter referred to by the variety name 'TMRO14-08'. The new variety of rose plant originated from an open pollination carried out by the inventor at the inventor's nursery in Ipswich, United Kingdom in 2011. The female parent is the inventor's proprietary variety known by code 'RO13197W' (unreleased, unpatented), and the male parent is an unknown proprietary variety from the inventor's collection of rose seedlings. Seeds collected from the female parent were sown, grown and planted in the field for evaluation.

The inventor selected and first propagated the new rose plant 'TMRO14-08' in 2014 in Ipswich, United Kingdom via softwood cuttings and has confirmed that 'TMRO14-08' reproduces true to type in successive generations of asexual propagation via softwood cuttings.

SUMMARY OF THE INVENTION

The following are the distinguishing characteristics of the new variety 'TMRO14-08' when grown under normal horticultural practices.

1. 'TMRO14-08' exhibits a semi-prostrate plant habit with pendulous branches when grown in containers.

2. 'TMRO14-08' bears small glossy green compound leaves.
3. The flowers of 'TMRO14-08' are semi-double.
4. Both surfaces of the inner petals of the flowers of 'TMRO14-08' are pale pink in color as the flower unfurls. The pink coloration disappears as the petals become pure white in color throughout as the flower fully opens and expands. The inner petals remain to present as pink colored centers to the fully open flowers. The inner petals bear a pink-colored basal spot.
5. The flowers of 'TMRO14-08' are self-cleaning.
6. 'TMRO14-08' bears glossy red hips when mature.
7. The flowers of 'TMRO14-08' are pleasantly fragrant.
8. 'TMRO14-08' is hardy in USDA Hardiness Zone 5.

These traits in combination distinguish 'TMRO14-08' from all other existing varieties of *Rosa* known to the inventor. 'TMRO14-08' has not been tested under all possible conditions and phenotypic differences may be observed with variations in environmental, climatic, and cultural conditions, without any variance in genotype.

BRIEF DESCRIPTION OF THE PHOTOGRAPH

The accompanying photograph illustrates the overall growth and flowering habit of 'TMRO14-08' at 24 months growing out of doors in Santa Barbara, California in a 20 cm. diameter container.

The photograph was made using conventional techniques and although flower and foliage color may appear different from actual color due to light reflectance, they are as accurate as possible by conventional photography. Colors in the photograph may differ slightly from the color values cited in the description, which accurately describes the observed colors of 'TMRO14-08'.

BOTANICAL DESCRIPTION OF THE PLANT

The following is a detailed botanical description of the new *Rosa* cultivar named 'TMRO14-08'. Observations and measurements were collected in August 2022 in Santa Barbara, California from a two year old plant growing outdoors in a 2-gallon container. Color determinations were made in accordance with The 2007 Royal Horticultural Society Colour Chart from London England, except where general color terms of ordinary dictionary significance are used. Growing requirements are similar to the species.

Botanical classification: *Rosa* x *hybrida* 'TMRO14-08'.

*Family*.—Rosaceae.

*Genus*.—*Rosa*.

*Species*.—x *hybrida*.

*Denomination*.—'TMRO14-08'.

*Common name*.—Shrub rose.

*Parentage*.—*Rosa* x *hybrida* 'TMRO14-08' is a seedling that resulted from the cross-pollination of the following parents: Female parent: Proprietary *Rosa* variety code 'RO13197W' (unpatented). Male parent: Unknown proprietary *Rosa* variety.

*Propagation method*.—Softwood cuttings.

Plant:

*Rooting system*.—Fine and fibrous.

*Root color*.—NN155D aging to 164D.

*Vigor*.—Moderate, remaining low-growing and compact.

*Habit*.—Semi-prostrate, pendulous branches.

*Use*.—For use in the garden and landscape and suitable for planting in containers and hanging baskets.

*Type*.—Perennial.

*Dimensions*.—After two year's growth from a rooted cutting, plants of 'TMRO14-08' are 60 cm. in width and 18 cm.-20 cm. in height.

*Cultural requirements*.—Grow in full sun with regular water, and well-draining media.

*Pest and disease resistance*.—No susceptibility to pests or diseases has been observed under local growing conditions.

*Hardiness*.—USDA Zone 5.

Stem and branches: When a rooted cutting is transplanted into the growing container, the cutting is pinched or stopped above the first node, creating a short basal stem at ground level. New growth develops from the basal stem (basal branching stems). All basal branching stems develop terminal inflorescences and bear lateral compound leaves.

*Basal stem*.—Shape: Cylindrical. Dimensions: Length 1 cm., diameter 0.8 cm.-1.0 cm. Color: 145A. Surface: Smooth.

*Branching stems*.—Shape: Cylindrical. Aspect: Arching, pendulous. Dimensions: Length 40 cm.-45 cm., diameter at base 5 mm. Color (first 7 cm. of stem from base): 144B. Color (above 7 cm. from base): 144B with anthocyanin coloration 183D present on solar-facing surfaces. Surface: Smooth.

*Internode length*.—Ranges between 2.5 cm. and 4.5 cm.

*Thorns*.—Description: Medium-sized thorns distributed along the entire length of the branches. Quantity: Average 30 per stem at average distance of 1 thorn per 1.5 cm. Aspect: Outward facing, pointing downwards. Shape: Deltoid with downward facing apical point, attachment to stem elliptic. Length: Predominantly 5 mm., occasionally up to 9 mm. Base dimensions: Length 5 mm.-7 mm., width 2.5 mm.-3.0 mm. Color: 59B.

Foliage:

*Description*.—Compound, consisting of 9 leaflets of which 4 leaflets arranged in opposite pairs and 1 terminal leaflet.

*Dimensions* (*overall, compound leaf including petiole*).—9.0 cm. in length, 3.5 cm. in width.

*Attachment* (*compound leaf*).—Petiolate.

*Petiole shape*.—Cylindrical with two opposite stipules attached longitudinally from petiole base towards first leaf pair.

*Petiole dimensions*.—22 mm. in length, 1.0 mm. in diameter.

*Petiole color* (*adaxial surface*).—60A.

*Petiole color* (*abaxial surface*).—146C.

*Petiole surface*.—Puberulent.

*Petiole thorns*.—Tiny, 1.0 mm.-1.5 mm. in length, pointing downwards, adaxially attached, one per leaflet node, color 59C.

*Stipule dimensions* (*each*).—14 mm. in length, 2.5 mm. in width at base, 1.0 mm. in width at apex.

*Stipule shape*.—Narrowly deltoid.

*Stipule apex*.—Free, acute.

*Stipule base*.—Truncate.

*Stipule color*.—145B.

*Stipule margins*.—Ciliate, cilia length 1.5 mm.-2.0 mm., color 136B.

*Stipule surface*.—Glabrous, except ciliate margins.

Leaflets:

*Quantity*.—9 leaflets (arranged as four opposite pairs and one terminal leaflet).

*Type*.—Evergreen.

*Shape*.—Obovate.

*Dimensions*.—Lowest or first leaflet pair, each leaflet: 18 mm. in length, 10 mm. in width. Second leaflet pair, each leaflet: 19 mm. in length, 14 mm. in width. Third leaflet pair, each leaflet: 18 mm. in length, 12 mm. in width. Fourth or uppermost leaflet pair: 21 mm. in length, 13 mm. in width. Terminal leaflet (single): 25 mm. in length, 15 mm. in width.

*Leaflet attachment*.—Petiolate (petiolules). Petiolule dimensions (all leaflets in pairs): 1.0 mm. in length, 0.5 mm in diameter. Petiolule dimensions (terminal leaflet): 8 mm. in length, 1.0 mm. in diameter. Petiolule surface: Smooth. Petiolule color: 60A (adaxial surface), 146C (abaxial surface).

*Leaflet color* (*adaxial surface*).—143A.

*Leaflet color* (*abaxial surface*).—138B.

*Leaflet base*.—Obtuse, occasionally oblique.

*Leaflet apex shape*.—Acute.

*Leaflet texture*.—Glabrous, glossy (adaxial surface), matte (abaxial surface).

*Leaflet margin*.—Serrate, teeth pointing towards apex, 14-18 teeth per leaflet edge, depth of teeth 0.5 mm.-1.0 mm.

*Venation*.—Reticulate. Veins (adaxial surface): Faintly visible as slight depressions, same color as leaflet. Veins (abaxial surface): Slightly raised, same color as leaflet, except midrib color 138D.

Inflorescence:

*Inflorescence type*.—Terminal panicle.

*Panicle arrangement*.—10-12 flowering branches per panicle. Branches bear flowers singly and in pairs alternately along stem.

*Inflorescence quantity*.—20-25 panicles per plant.

*Flower and bud quantity*.—Approximately 40 flowers and buds per panicle, 80-100 flowers and buds per plant.

*Dimensions of inflorescence* (*average*).—20 cm. in length, 14 cm. in width.

*Blooming seasons*.—Spring through fall. Flower production is increased by removal of spent flowers.

*Bud*.—Shape: Pointed ovoid. Dimensions (immediately prior to petal color first showing): 9 mm. in height and 8 mm. in diameter. Color: Between RHS 143C and 143D.

*Sepals*.—Quantity: 5, inwardly curved. Sepal shape: Deltoid with fine extended acuminate apex, fused towards base. Sepal extension dimensions: 1.5 mm in length, less than 0.5 mm in width or diameter. Sepal extension color: 187C. Sepal dimensions: Length (including acuminate apex) 9 mm., width 3 mm. at fused base. Sepal color (both surfaces): Ranges between 143C and 143D. Sepal surface (adaxial): Smooth with short fine erect hairs, hair length less than 0.5 mm., hair color 187A. Sepal surface (abaxial): Glabrous. Sepal margin: Puberulent.

*Receptacle* (*after removal of sepals*).—Shape: Flat-topped globular. Dimensions: 6 mm in diameter, 4 mm in height. Color: Inward-facing surface 182A; outward-facing surface 139C. Surface: Smooth, matte.

*Peduncle*.—Shape: Cylindrical. Dimensions: 8 mm.-11 mm. in length, 1.0 mm.-1.5 mm. in diameter. Color: N187A. Surface: Smooth with fine short sharp stiff thorns, less than 1 mm. in length, color N187A.

*Blooms*.—Size: 4.0 cm.-4.5 cm. in diameter, 1.5 cm. in height. Type, shape, and arrangement: Semi-double shallow cupped flowers borne singly as terminal flowers in each panicle, borne in pairs or singly below, in each panicle axil. Lower portion of bloom concave in profile, upper portion flatted or slightly raised, convex in profile. Fragrance: Slight and pleasant, typical of scented roses. Lastingness: Individual blooms are short-lasting once fully open, around 4 days on the plant and 3 days off the plant. Blooms are self-cleaning: petals shatter and fall away.

*Petals*.—Arrangement: Typically 5 fully-formed petals in each of 5 closely arranged layered whorls. Number: Approximately 40 per bloom. Form: Inwardly recurved. Shape: Obcordate. Approximately six larger petals appear as two lobes longitudinally fused. Dimensions: Averages 17 mm. in length, 16 mm. in width. Larger petals 19 mm. in length, 20 mm. in width. Base: Mostly obtuse, larger petals cordate. Basal spot: Present on early developing inner petals and visible when petals are detached. Spot is evident on petal adaxial surface close to (3 mm from) petal base. Basal spot appears as three distinct and separate parallel short narrow lines, length 1 mm, and 1.5 mm apart and width less than 0.25 mm. Spot or narrow line color light purple-pink 64D. Apex: Acute. Texture: Delicate, translucent towards margins, glabrous. Margins: Smooth, entire. Color (inner petals as flowers unfurls): 55D, lighter N155A in center. Color (both surfaces, bloom aged and petals about to drop): NN155D.

*Petaloids*.—Description: Multiple petaloids arising around and from within the reproductive organs. Petaloids emerge darker pink than petals. Number: Approximately 16 per bloom. Form: Inwardly recurved. Shape: Variable, nonsymmetrical, many contorted or twisted. Dimensions: 7 mm.-10 mm. length, 3 mm.-5 mm. width. Base: Acute. Apex: Rounded or emarginate. Texture: Delicate, translucent towards margins, glabrous. Margins: Smooth, entire. Petaloid color (both surfaces, bloom freshly open):55D, 55C toward petaloid base. Color (both surfaces, bloom aged and petals about to drop): NN155D.

Reproductive organs:

*Stamens*.—Number: 35-40. Arrangement: Radiating around bundle of pistils. Filaments 4 mm.-5 mm. in length, less than 0.5 mm. in diameter. Filament color: 12B.

*Anthers*.—Shape, dimensions: Truncated ellipsoid, length 1 mm., width 0.5 mm. Attachment: Dorsifixed. Color (freshly opened blooms): 163C. Color (senescent blooms): 202A.

*Pollen*.—Moderate amount, grains approximately 0.25 mm.-0.5 mm. in diameter. Color: 25A.

*Pistil*.—Description: One, consisting of a bundle of basally fused styles and free style apices bearing very small stigmas. Style: Dimensions (bundle of 35-40 in number): 4 mm. in length, less than 0.25 mm. in diameter. Color: 142B (base), 12B (free). Stigmas: Dimensions: Very small, indistinguishable from free styles. Color: 12B. Ovary (observed immature): Shape: Globular. Dimensions: 1.5 mm. in diameter. Color: 145C.

Fruit (hips):

*Quantity*.—Numerous: all flowers have been fertilized or self-fertilized and formed hips.

*Shape*.—Spherical, flattened apex.

*Diameter* (*when ripe*).—9 mm.

*Color*.—138B (juvenile hips), 185A (semi-ripe hips), ranging between 42A and 42B when fully ripe.

*Surface*.—Glabrous and glossy.

Seed:

*Quantity*.—25 seeds per hip.

*Shape*.—Rounded tetragonal.

*Dimensions*.—4 mm. in height, 3 mm. in width.

*Color* (*observed immature only*).—12B.

COMPARISON WITH SIMILAR COMMERCIAL VARIETY

'TMRO14-08' can be compared to the commercial variety 'Meiggili' (U.S. Plant Pat. No. 18,542) as described below in Table 1:

TABLE 1

Comparison with Similar Variety

| Characteristic | 'TMRO14-08' | 'Meiggili' |
|---|---|---|
| Habit | Semi-prostate | Spreading |
| Flowers | Semi-double | Double |
| Foliage | Dark green, glossy | Dark green, glossy |

TABLE 1-continued

| Comparison with Similar Variety | | |
|---|---|---|
| Characteristic | 'TMRO14-08' | 'Meiggili' |
| Flower color | Initially pink with darker pink centers, becoming pure white | Peach |

COMPARISON WITH PARENT

'TMRO14-08' can only be compared to the female parent variety 'RO13197W' as described below in Table 2:

TABLE 2

| Comparison with Female Variety | | |
|---|---|---|
| Characteristic | 'TMRO14-08' | RO13197W |
| Habit | Semi-prostrate, pendulous branching | Mounding, upright branching |
| Flowers | Semi-double | Double |
| Flower color | Initially light pink with darker pink centers, becoming pure white | Light pink |

I claim:

1. A new and distinct cultivar of Shrub Rose Plant Named 'TMRO14-08' as described and illustrated herein.

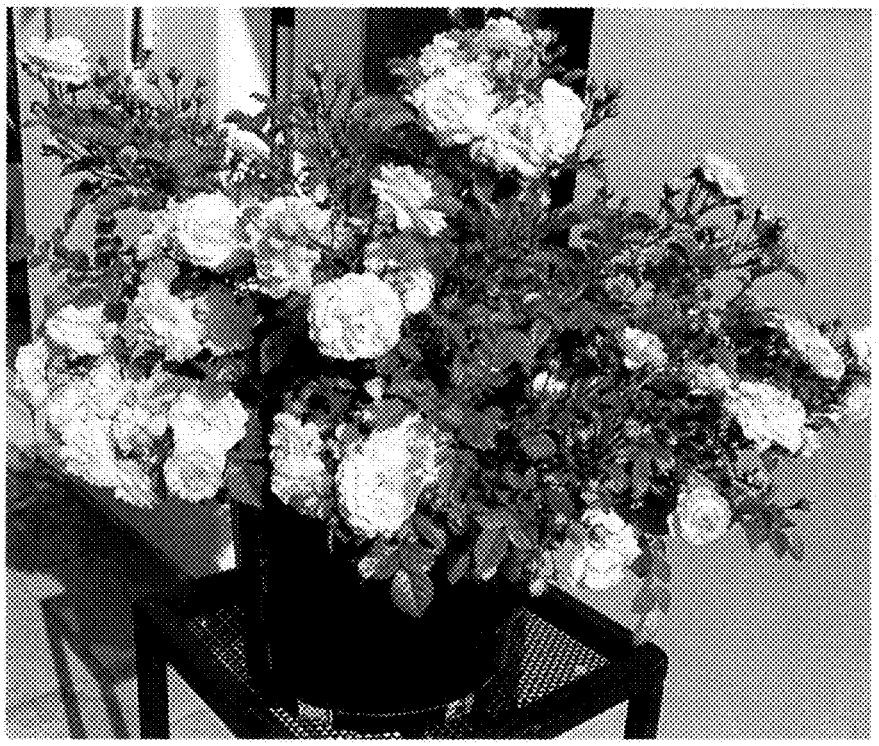

* * * * *